(12) United States Patent
Kuo et al.

(10) Patent No.: US 7,870,959 B2
(45) Date of Patent: Jan. 18, 2011

(54) SELF-SEALED MEDICAL STERILIZATION POUCH

(75) Inventors: Dewitt Kuo, Jui-Fang Chen (TW); Thomas Chou, Jui-Fang Chen (TW)

(73) Assignee: Signma Medical Supplies Corp., Taipei (TW)

( * ) Notice: Subject to any disclaimer, the term of this patent is extended or adjusted under 35 U.S.C. 154(b) by 21 days.

(21) Appl. No.: 12/481,651

(22) Filed: Jun. 10, 2009

(65) Prior Publication Data

US 2010/0108551 A1    May 6, 2010

(30) Foreign Application Priority Data

Oct. 31, 2008    (TW) ............... 97219503 U

(51) Int. Cl.
*B65D 85/00*    (2006.01)
(52) U.S. Cl. .................. 206/459.1; 206/363; 206/438; 422/26; 422/58; 422/119
(58) Field of Classification Search ............. 206/363, 206/438, 439, 459.1, 459.5, 570–572; 116/206, 116/209; 383/107; 422/26, 27, 55, 58, 102, 422/119, 290
See application file for complete search history.

(56) References Cited

U.S. PATENT DOCUMENTS

| | | | | |
|---|---|---|---|---|
| 3,991,881 A | * | 11/1976 | Augurt | 206/439 |
| 4,121,714 A | * | 10/1978 | Daly et al. | 206/363 |
| 4,176,746 A | * | 12/1979 | Kooi | 206/438 |
| 4,194,622 A | * | 3/1980 | Lewis | 206/363 |
| 4,276,982 A | * | 7/1981 | Sibrava et al. | 206/439 |
| 5,344,017 A | * | 9/1994 | Wittrock | 206/459.1 |
| 5,727,686 A | * | 3/1998 | Kristal | 206/459.1 |
| 7,237,676 B2 | * | 7/2007 | Celia | 206/459.1 |
| 2009/0123332 A1 | * | 5/2009 | Whitehead et al. | 422/27 |

* cited by examiner

*Primary Examiner*—Luan K Bui
(74) *Attorney, Agent, or Firm*—Roger H. Chu

(57) ABSTRACT

A self-sealed medical sterilization pouch comprises the following elements of: a first sheet being pervious to sterilization gases and surrounded by at least one printing domain thereon, a plurality of signs being disposed on the printing domain and located outside of a closed space, the first sheet having at least two sterile processing indicators having color response, one surface of an end of the first sheet having a flap; and a second sheet being impervious to sterilization gases, the second sheet having an opening and being joined with the first sheet by a first seal line, a second seal line and a third seal line at a left side, a right side and an upper side to form the closed space, the sterile processing indicators being disposed between the third seal line and a ladle-shaped end and the third seal line and another ladle-shaped end respectively.

6 Claims, 4 Drawing Sheets

SELF-SEALED MEDICAL STERILIZATION POUCH

BACKGROUND OF THE INVENTION

1. Field of Invention

The invention relates to sterilization pouches and more particularly to a self-sealed medical instrument sterilization pouch.

2. Description of Related Art

Medical instruments have to be gathered after use, cleaned, packaged in sterilizable pouches. Medical instruments are sealed in a closed space defined by the pouch walls, and then subjected to a sterilizing environment such as steam or high temperature water vapor used to sterilize the instruments. Besides, the pouch-enclosed instruments are subjected to a sterilizing gas such as ethylene oxide.

The sealed pouches comprise a lower sheet and an upper sheet. The lower sheet is typically planar sheet material, suitably cellulosic in composition and printable, and pervious to steam, water vapor and sterilization gases. The upper sheet is planar, but typically of transparent plastic such as polyester, impervious to water vapor, steam and sterilizing gases. Moreover, to make sure that a given pouch has been sterilized, indicators are used. One way to make sure that a given pouch has been sterilized is to provide a separate indictor-strip into the pouch. Besides, the indicators typically are printing inks having color change response to steam, high temperature water vapor or a sterilizing gas such as ethylene oxide, or other sterilizing agent. For example, the ink permanently changes from gray to brown when exposed to sterilizing conditions.

Conventional sterilizing pouches are formed of sheet material printed with identifying brand names and other information on an outward face, and the indictor ink has been placed on the same face. In addition, in order to protect ink dot from deleterious frictional contact with the medical instruments, a protective barrier is preferably provided between the dot and the medical instruments. The barrier is integrated into a seal line by bifurcating the seal line at the apex thereof to form a diamond-shaped enclosure within which the indictor ink dot is placed.

However, the conventional sterilizing pouches have several drawbacks. First, the conventional sterilizing pouches are lack of protection for the ink from frictional removal during handling and storage. Medical instruments may be contaminated by ink. Second, the separate indictor-strip is easy to be polluted. Finally, the conventional sterilizing pouches have a V-shaped seal line to form the barrier, but the seal line is easy to be breached by the medical instruments during handling and storage. Thus, the need for improvement still exists.

SUMMARY OF THE INVENTION

It is therefore one object of the invention to provide a self-sealed medical sterilization pouch, which comprises the following elements of: a first sheet being pervious to steam, water vapor and sterilization gases and surrounded by at least one printing domain thereon, a plurality of signs being disposed on the printing domain and located outside of a closed space which is for medical sterilization in order to keep the area of the first sheet covered by the closed space clean, the first sheet having at least two sterile processing indicators having color response to the medical sterilization thereon, one surface of an end of the first sheet having a flap, a folding line being between the first sheet and the flap; and a second sheet being impervious to steam, water vapor and sterilization gases, at least one medical instrument being accommodated in a predetermined position of the closed space, wherein the closed space is between the first sheet and the second sheet, the second sheet having an opening and being joined with the first sheet by a first seal line, a second seal line and a third seal line at a left side, a right side and an upper side to form the closed space, wherein the opening is toward the flap, around the third sealed line closed to the upper side being a shortest seal line, which comprises an arched portion and two ladle-shaped ends and is not connected to the first seal line, the second seal line and the third seal line, the printing domain being surrounded and blocked by the first seal line and the second seal line while the first sheet and the second sheet are joined with each other, the sterile processing indicators being disposed between the third seal line and the ladle-shaped end and the third seal line and the ladle-shaped end respectively.

In one aspect of the invention the sterilization gas comprises ethylene oxide.

In another aspect of the invention the second sheet is made of plastic.

In a further aspect of the invention the sterile processing indicators are two sterile ink dots and separately responsive to different pairs of sterilizing agents.

In another further aspect of the invention the second sheet comprises a gap formed at one end of the second sheet.

By utilizing the invention, the following advantages are obtained. First, the invention provides a self-sealed medical sterilization pouch. The third sealed line comprises an arched portion and two ladle-shaped ends. Thus, the pouch utilizes protecting seal at chevron side to prevent packed item's breaching by medical instruments. The third sealed line can effectively prevent the medical instruments from contacting the ink.

Second, the second sheet is made of non-tearing film. It is a superior film to have complete film separation at any speed or condition opening, without shearing and tearing, to maintain clean-opening aseptically.

Third, the first sheet is made of first grade medical paper. The medical grade paper provides optimal barrier properties and offers higher level security.

Fourth, the present invention utilizes printed-in internal indicator. The indicator can fulfill pouch-inside sterilant contacting and self-sealed pouches, additionally, can save on putting separate indicator-strip into pouch and free of polluting.

Fifth, in order to assure sterility sterilization, packed items should be sterilized to three sterilization parameters: time, temperature and sterilant contact. The present invention is followed by ISO standards and CDC infection control guidelines. Finally, free-polluted printing is used. The present invention uses water-based ink and printed outside actual packing area. It can be free of polluting on packed items.

The invention will become more obvious from the following description when taken in connection with the accompanying drawings.

DETAILED DESCRIPTION OF THE INVENTION

Figure 1:
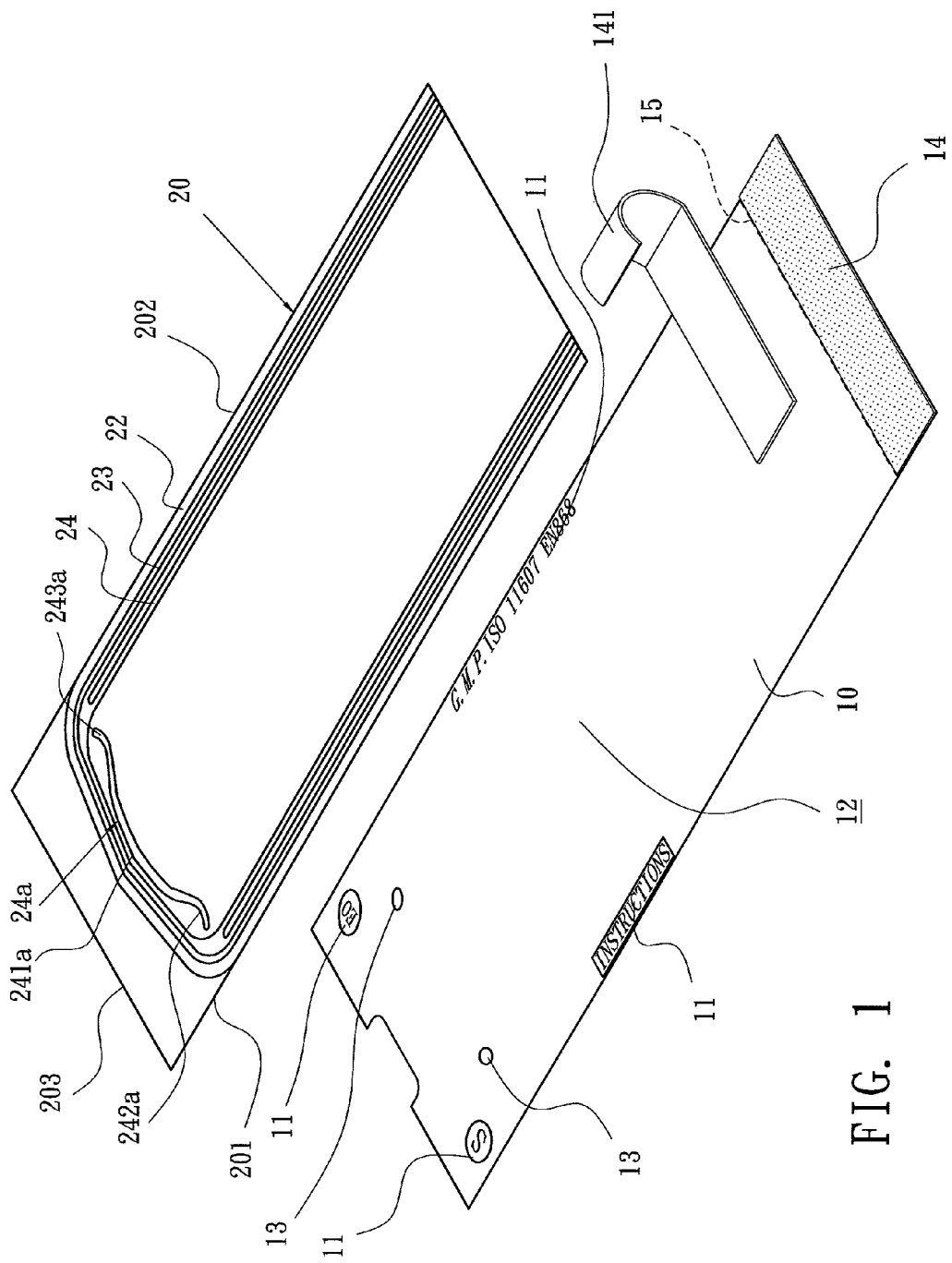
FIG. 1 is an exploded view of a preferred embodiment of a self-sealed medical sterilization pouch according to the invention.
Figure 2:
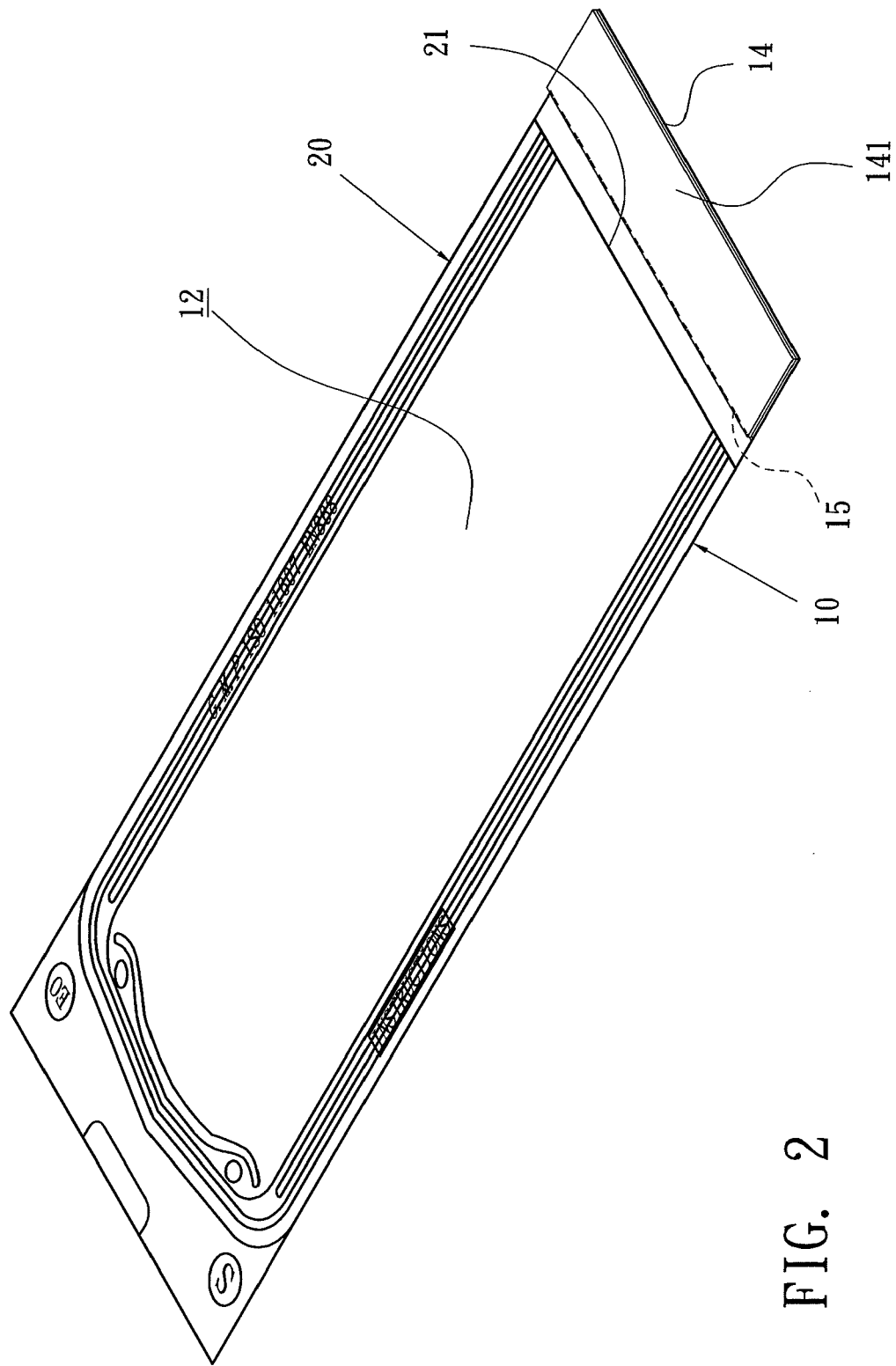
FIG. 2 is a perspective view of the self-sealed medical sterilization pouch according to the invention.
Figure 3:
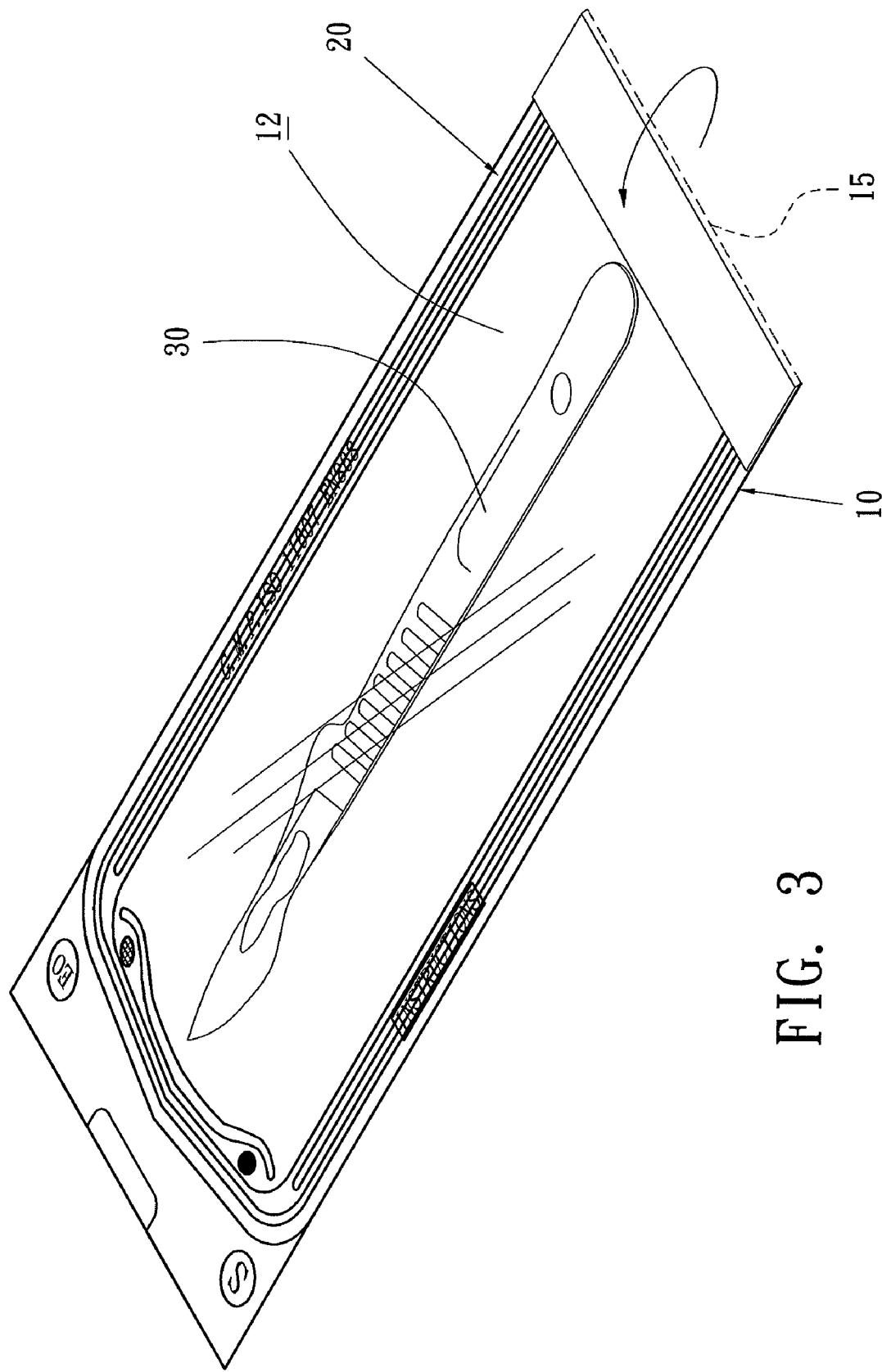
FIG. 3 is a view of the self-sealed medical sterilization pouch containing medical instruments inside according to the invention.
Figure 4:
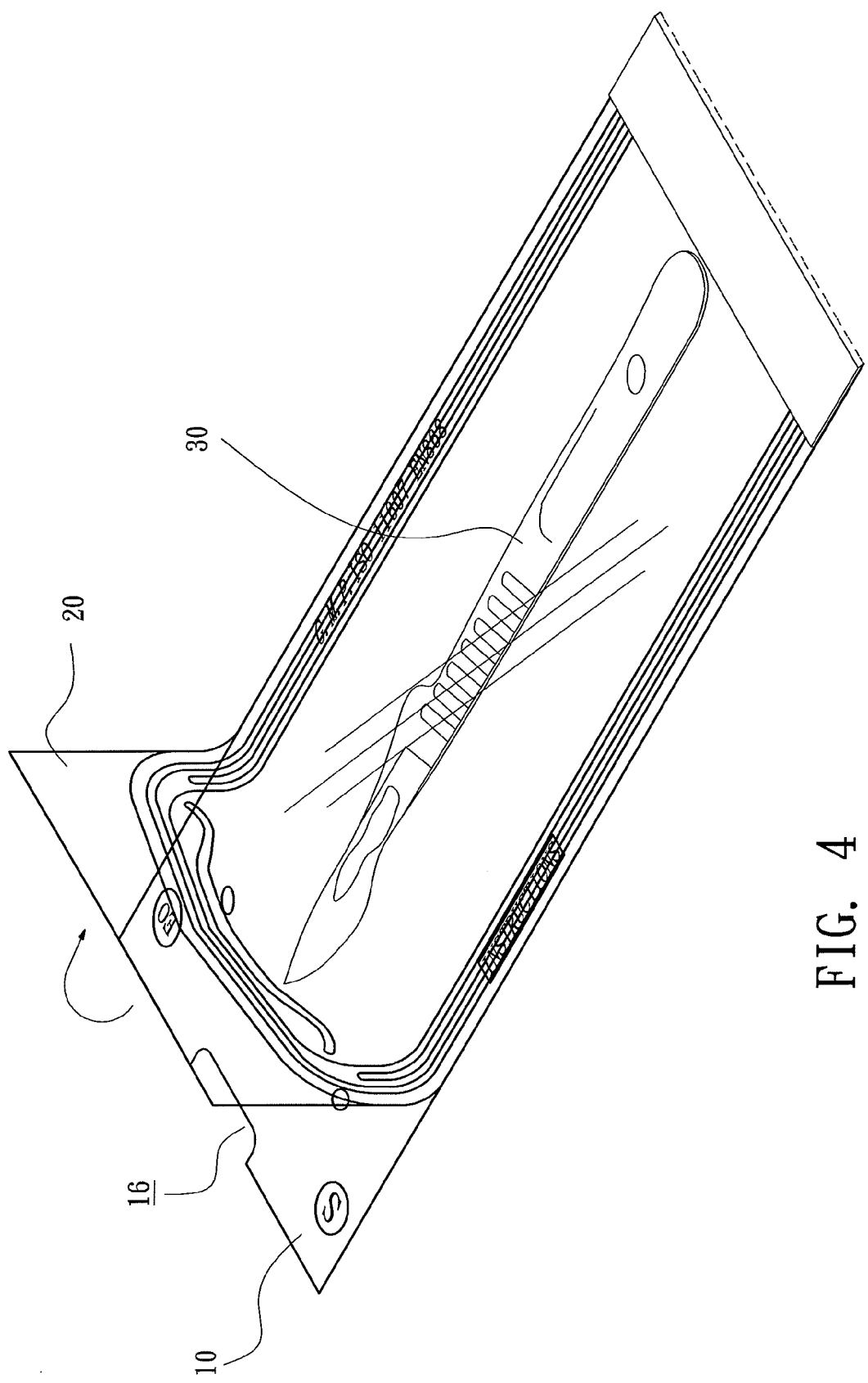
FIG. 4 is a view of how to open the self-sealed medical sterilization pouch containing medical instruments inside according to the invention.

Referring to FIGS. 1 to 4, a self-sealed medical sterilization pouch in accordance with a preferred embodiment of the invention is shown. The present invention is to provide the self-sealed medical sterilization pouch and includes: a first sheet 10 and a second sheet 20. The first sheet 10 is pervious to steam, water vapor and sterilization gases and surrounded by three printing domains 11 thereon, a plurality of signs as words or other symbols are disposed on the printing domains 11 and located outside of a closed space 12 which is for medical sterilization in order to keep the area of the first sheet 10 covered by the closed space 12 clean, the first sheet 10 has two sterile processing indicators 13 having color response to the medical sterilization thereon, one surface of an end of the first sheet 10 has a flap 14, a folding line 15 is between the first sheet 10 and the flap 14. The second sheet 20 is impervious to steam, water vapor and sterilization gases, a medical instrument 30 is accommodated in a predetermined position of the closed space 12, wherein the closed space 12 is between the first sheet 10 and the second sheet 20, the second sheet 20 has an opening 21 and is joined with the first sheet 10 by a first seal line 22, a second seal line 23 and a third seal line 24 at a left side 201, a right side 202 and an upper side 203 to form the closed space 12, wherein the opening 21 is toward the flap 14, around the third sealed line 24 closed to the upper side 203 is a shortest seal line 24a, which includes an arched portion 241a and two ladle-shaped ends 242a and 243a and is not connected to the first seal line 22, the second seal line 23 and the third seal line 24, the printing domain 11 being surrounded and blocked by the first seal line 22 and the second seal line 23 while the first sheet 10 and the second sheet 20 are joined with each other, the sterile processing indicators 13 are disposed between the third seal line 24 and the ladle-shaped end 242a and the third seal line 24 and the ladle-shaped end 243a respectively, The first sheet 10 is made of first grade medical paper. The medical grade paper provides optimal barrier properties and offers higher level security.

The second sheet 20 is made of non-tearing film. It is a superior film to have complete film separation at any speed or condition opening, without shearing and tearing, to maintain clean-opening aseptically. Thus, the pouch utilizes protecting seal at chevron side to prevent packed item's breaching by the medical instrument 30. The third sealed line 24 can effectively prevent the medical instrument 30 contacting ink.

The flap 14 on the second sheet 20 is arranged to overlie the first sheet 10 in seal for fully enclosing the closed space 12, wherein the two sterile processing indicators 13 are adjacent to the second seal line 23 and the third seal line 24, the two sterile processing indicator 13 are surrounded by the second seal line 23 and the ladle-shaped end 242a and 243a respectively. The indicator 13 can fulfill pouch-inside sterilant contacting and self-sealed pouch, additionally, can save on putting separate indicator-strip into pouch and free of polluting. The flap 14 includes a protecting paper 141 and the folding line 15. The flap 14 is adhesive to the second sheet 20 while the protecting paper 141 is tore off and the folding line 15 is folded up, so that the closed space 12 is completely sealed.

Preferably, the sterilization gases can be ethylene oxide, hydrogen peroxide gas, inorganic agents, organic agents suitable, etc. for such purposes.

Preferably, the second sheet 20 is made of plastic.

Preferably, the sterile processing indicators 13 are two sterile ink dots and separately responsive to different sterilizing agents. The inks used to print the sterile ink dots are conventional in the industry for monitoring sterilization exposure to various sterilants.

Preferably, the second sheet 20 includes a gap 16 formed at one end of the second sheet 20. The gap 16 can separate the first sheet 10 from the second sheet 20 easily.

The present invention thus provides an improved sterilization and storage pouch for medical instruments having two indicators thereon protected from being pierced and breached.

While the invention herein disclosed has been described by means of specific embodiments, numerous modifications and variations could be made thereto by those skilled in the art without departing from the scope and spirit of the invention set forth in the claims.

What is claimed is:

1. A self-sealed medical sterilization pouch comprising:
a first sheet being pervious to steam, water vapor and sterilization gases and surrounded by at least one printing domain thereon, a plurality of signs being disposed on the printing domain and located outside of a closed space which is for medical sterilization in order to keep the area of the first sheet covered by the closed space clean, the first sheet having at least two sterile processing indicators having color response to the medical sterilization thereon, one surface of an end of the first sheet having a flap, a folding line being between the first sheet and the flap; and
a second sheet being impervious to steam, water vapor and sterilization gases, at least one medical instrument being accommodated in a predetermined position of the closed space, wherein the closed space is between the first sheet and the second sheet, the second sheet having an opening and being joined with the first sheet by a first seal line, a second seal line and a third seal line at a left side, a right side and an upper side to form the closed space, wherein the opening is toward the flap, around the third seal line close to the upper side being a shortest seal line, which comprises an arched portion and two ladle-shaped ends and is not connected to the first seal line, the second seal line and the third seal line, wherein the arched portion and two ladle-shaped ends are connected to each other, the printing domain being surrounded and blocked by the first seal line and the second seal line while the first sheet and the second sheet are joined with each other, the sterile processing indicators being disposed between the third seal line and the ladle-shaped end and the third seal line and the ladle-shaped end respectively.

2. The pouch of claim 1, wherein the sterilization gas is selected from a group consisting of: ethylene oxide, hydrogen peroxide gas, inorganic agents, and organic agents.

3. The pouch of claim 1, wherein the second sheet is made of non-tearing film.

4. The pouch of claim 1, wherein the second sheet is made of plastic.

5. The pouch of claim 1, wherein the sterile processing indicators are two sterile ink dots and separately responsive to different sterilizing agents.

6. The pouch of claim 1, wherein the second sheet comprises a gap formed at one end of the second sheet.

* * * * *

UNITED STATES PATENT AND TRADEMARK OFFICE
CERTIFICATE OF CORRECTION

| | | |
|---|---|---|
| PATENT NO. | : 7,870,959 B2 | Page 1 of 1 |
| APPLICATION NO. | : 12/481651 | |
| DATED | : January 18, 2011 | |
| INVENTOR(S) | : Dewitt Kuo and Thomas Chou | |

It is certified that error appears in the above-identified patent and that said Letters Patent is hereby corrected as shown below:

on the title page

(73) Assignee:    the word "SIGNMA" should read --SIGMA--

Signed and Sealed this
Twelfth Day of April, 2011

David J. Kappos
*Director of the United States Patent and Trademark Office*